(12) United States Patent
Liebsch et al.

(10) Patent No.: US 9,976,956 B2
(45) Date of Patent: May 22, 2018

(54) METHOD FOR DETERMINING A VARIABLE OF A SAMPLE

(71) Applicant: PreSens—Precision Sensing GmbH, Regensburg (DE)

(72) Inventors: Gregor Liebsch, Obertraubling (DE); Damian Andrzejewski, Sinzing (DE)

(73) Assignee: PreSens—Precision Sensing GmbH, Regensburg (DE)

( * ) Notice: Subject to any disclaimer, the term of this patent is extended or adjusted under 35 U.S.C. 154(b) by 0 days. days.

(21) Appl. No.: 15/044,741

(22) Filed: Feb. 16, 2016

(65) Prior Publication Data

US 2016/0161408 A1    Jun. 9, 2016

Related U.S. Application Data

(63) Continuation of application No. PCT/IB2014/063765, filed on Aug. 7, 2014.

(30) Foreign Application Priority Data

Aug. 21, 2013  (DE) .................. 10 2013 109 010

(51) Int. Cl.
   *G01N 21/64*   (2006.01)
   *G01K 11/20*   (2006.01)
(52) U.S. Cl.
   CPC ......... *G01N 21/6408* (2013.01); *G01K 11/20* (2013.01)
(58) Field of Classification Search
   CPC .................................. G01N 21/6408
   See application file for complete search history.

(56) References Cited

U.S. PATENT DOCUMENTS 5,043,585 A * 8/1991 Fehrenbach ....... G01K 11/3213
                                                    250/458.1
5,304,809 A    4/1994 Wickersheim
                     (Continued)

FOREIGN PATENT DOCUMENTS

DE        19634873       3/1998
DE        101 52 994     8/2003
                     (Continued)

OTHER PUBLICATIONS

"Fluorescent Imaging of pH with Optical Sensors Using Time Domain Dual Lifetime Referencing" by G. Liebsch, I. Klimant, C. Krause, and O. S. Wolfbeis in Analytical Chemistry vol. 73, No. 17, Sep. 1, 2001, pp. 4354 to 4363.
(Continued)

*Primary Examiner* — David Porta
*Assistant Examiner* — Djura Malevic
(74) *Attorney, Agent, or Firm* — Davidson, Davidson & Kappel, LLC

(57) ABSTRACT

A method for determining a variable of a sample is provided. At least one sensor substance is brought into contact with the sample and excited to luminesce by means of an electromagnetic excitation signal. The sensor substance is such that a relaxation time of its luminescence behavior depends on the variable of the sample to be determined. The electromagnetic excitation signal has a defined time-dependence, it is, for example, a frequency-modulated signal or a pulse sequence, in which distances between pulses are varied over the duration of the excitation signal. The time dependence of the luminescence response of the sensor substance is detected and an output signal is generated therefrom by integrating over specified time-intervals. An instant of time, relative to the time-dependence of the excitation signal, is determined, at which a step occurs in the time-dependence (Continued)

of the output signal. The value of the variable is determined from said instant of time. A preceding calibration can be advantageously used for this purpose.

20 Claims, 3 Drawing Sheets

(56) References Cited

U.S. PATENT DOCUMENTS

| | | | |
|---|---|---|---|
| 5,315,993 A | 5/1994 | Ricardo | |
| 5,485,530 A * | 1/1996 | Lakowicz | G01K 11/20 250/459.1 |
| 6,140,048 A | 10/2000 | Muller et al. | |
| 7,044,634 B2 * | 5/2006 | Sandvoss | G01N 25/72 374/121 |
| 7,852,473 B2 * | 12/2010 | Wolff | G01N 21/6456 356/244 |
| 8,759,793 B2 * | 6/2014 | Giesecke | G01N 21/6408 250/459.1 |
| 9,316,585 B2 * | 4/2016 | Liebsch | G01N 21/6408 |
| 2005/0075575 A1 * | 4/2005 | Vo-Dinh | A61B 5/0059 600/476 |
| 2007/0267581 A1 * | 11/2007 | Roth | G01N 21/6408 250/458.1 |
| 2010/0267049 A1 * | 10/2010 | Rutter | G01N 21/6428 435/7.1 |
| 2013/0140431 A1 | 6/2013 | Lacroix | |
| 2014/0306125 A1 | 10/2014 | Liebsch | |

FOREIGN PATENT DOCUMENTS

| | | |
|---|---|---|
| DE | 10 2011 055 272 | 5/2013 |
| EP | 0 442 060 | 8/1991 |

OTHER PUBLICATIONS

"Luminescence Lifetime Imaging of Oxygen, pH, and Carbon Dioxide Distribution Using Optical Sensors" by G. Liebsch, I. Klimant, B. Frank, G. Hoist, and O. S. Wolfbeis in Applied Spectroscopy 54, No. 4 (2000), pp. 548 to 559.

"Fluorescent Imaging of pH with Optical Sensors Using Time Domain Dual Lifetime Referencing" by G. Liebsch, I. Klimant, C. Krause, and O. S. Wolfbeis in Analytical Chemistry vol. 73, No. 17, Sep. 1, 2001, pp. 4354 to 4363, Abstract submitted.

\* cited by examiner

METHOD FOR DETERMINING A VARIABLE OF A SAMPLE

This is a Continuation of International Patent Application No. PCT/IB2014/063765, filed Aug. 7, 2014 which claims the benefit of German Patent Application DE 10 2013 109 010.9, filed Aug. 21, 2013, both of which are hereby incorporated by reference herein.

The present invention relates to a method for determining a variable of a sample, more specifically to a method in which the variable of the sample is determined from the luminescence behavior of a sensor substance.

BACKGROUND

The German published patent application DE 196 34 873 A1 describes an apparatus and a method for discriminating, by a time-resolved fluorescence measurement, at least two differently fluorescing types of molecule groups bound to analyte molecules. Therein a light source for illuminating a sample volume is activated for a time-interval $T_1$, then, after a time-interval $T_2$, a detector is activated for a time $T_3$. Which of the at least two molecule groups are contained in the sample volume is determined from the time-dependence of the detector signals recorded in the time-interval $T_3$.

The U.S. Pat. No. 5,315,993 discloses a probe and an apparatus for monitoring a plurality of parameters in an environment by making use of a luminescence phenomenon. To this end a luminescence dye is illuminated with a plurality of excitation light components, the amplitudes of which are modulated in time at specific modulation frequencies. The luminescence response comprises a plurality of luminescence light components, which show modulations corresponding to the modulations of the excitation light. Spectral data resulting from a Fourier-transformation enter model equations from which, inter alia, the life-time of individual luminescence light components can be determined.

The German published patent application DE 101 52 994 A1 describes a method for simultaneously optically determining pH-value and oxygen in solution for a mainly aqueous sample. Therein a single sensor matrix is used, which contains at least two indicator dyes providing at least one distinguishable optical signal for the quantities pH-value and oxygen in solution. In one disclosed embodiment of the method pH-value and oxygen in solution are determined by measuring the relaxation time of a fluorescence response of the indicators following a pulsed excitation.

The European patent application EP 0 442 060 A2 relates to a ratiometric luminescence measurement for determining a variable, for example the concentration of a substance. To this end a first luminescent material with a first absorption band and a second luminescent material with a second absorption band are used; the first and second absorption band do not overlap completely. In alternating first and second illumination intervals the luminescent materials are illuminated with a first excitation light within the first, but outside of the second absorption band, and with a second excitation light within the second, but outside of the first absorption band, respectively. The corresponding luminescence responses of the first and second luminescent material, detected during first and second response intervals, respectively, are evaluated and used for determining the variable.

The article "Luminescence Lifetime Imaging of Oxygen, pH, and Carbon Dioxide Distribution Using Optical Sensors" by G. Liebsch, I. Klimant, B. Frank, G. Holst, and O. S. Wolfbeis in Applied Spectroscopy 54, number 4 (2000), pages 548 to 559, describes the determination of various variables for samples in the wells of a microtiter plate via the dependence of the fluorescence life-time of materials used as sensor on the respective variable. The fluorescence life-time is found as follows: the fluorescence is excited by a light pulse, after the end of which the fluorescence response of the sensors is respectively integrated over two temporally distant intervals of preferentially same duration. The fluorescence life-time is determined from the ratio of the integral values thus obtained. Compared with methods based solely on intensity, this ratiometric method, based on a ratio of measured quantities, has the advantage of being practically independent of local absolute values of the excitation energy.

The article "Fluorescent Imaging of pH with Optical Sensors Using Time Domain Dual Lifetime Referencing" by G. Liebsch, I. Klimant, C. Krause, and O. S. Wolfbeis in Analytical Chemistry Vol. 73, No. 17, Sep. 1, 2001, pages 4354 to 4363, relates to the determination of the pH-distribution in microtiter plates and on a surface. A combination of two luminescent materials, where the ratio of the amounts of the materials is fixed, is used: one fluorescent material, the fluorescence decay-time of which depends on the pH-value, and one phosphorescent material, the phosphorescence decay-time of which is independent of the pH-value. The luminescent materials are excited by illumination, and during the excitation, within a first interval, the combined fluorescence and phosphorescence response of the materials is integrated. Immediately after the end of the excitation the recording of the luminescence response of the materials is interrupted for a period of time which is long enough for the fluorescence to decay practically completely. Afterwards, during a second time interval, which preferentially is of equal length to the first interval, the phosphorescence response of the phosphorescent material is integrated. From the ratio of the two values of the integrals eventually the pH-value can be inferred.

The German published patent application DE 10 2011 055 272 A1 describes a method for determining at least one parameter of a system, wherein the at least one parameter depends on at least one relaxation time of the system. The system is excited by a first sequence of electromagnetic excitation pulses, the sequence having a first defined time gap between consecutive excitation pulses. The response of the system to the first sequence of excitation pulses is integrated continuously over time, and in this way a first response-signal is generated. Likewise, by continuous integration over time of at least a second response of the system a second response-signal is generated. The at least one parameter is determined taking into account the first response-signal and the at least one second response-signal. Preferentially this involves the formation of a ratio of the first and the at least one second response-signal. The system may comprise an object and a sensor means having at least one relaxation time depending on a variable of the object. The parameter, and thus, as the case may be, the variable, may be determined in a space-resolved manner.

Luminescence-based measuring methods are known for the detection and the quantitative determination of many analytes. If the method is based on the intensity of the luminescence phenomenon, a reproducible illumination of the sample studied, in case of the illumination of an area for an extended sample also the spatial homogeneity of the illumination, is crucial. Other methods are based on the decay-time of the luminescence phenomenon, and exploit the fact that this decay-time in case of numerous luminescent materials depends on specific variables of the environment; examples of such variables are pH-value, concentration of a substance, or temperature. With these methods, for which the prior art cited above contains examples, the luminescence response of a substance used as a sensor material is integrated over defined time intervals, and a ratio of the values of the integrals thus obtained is formed. By this formation of a ratio, due to which the methods are classified as ratiometric, the dependence on fluctuations of the illumination is considerably reduced. With these methods it is not necessarily the decay-time or relaxation time of the luminescence phenomenon which is determined explicitly, but instead often a parameter which depends on the relaxation time, for example the ratio of the mentioned values of integrals. If a respective variable to be determined is calibrated against a corresponding respective parameter, the value of the variable can be found from the luminescence response. A difficulty with these methods, however, is to implement the defined time intervals for the integration of the luminescence response with sufficient precision in the measurement apparatus. This involves a certain technical effort implying corresponding costs. Furthermore the technology used is very sensitive, which makes its use, in particular for portable devices in the field, problematic, in particular again with respect to costs.

SUMMARY OF THE INVENTION

It is an object of the invention to provide a method for determining a variable of a sample in a simple way, in particular not requiring much effort in its performance.

The present invention provides that first a contact is established between at least one sensor substance and the sample. Each sensor substance used therein has a luminescence behavior with a relaxation time depending on the variable of the sample to be determined. Luminescence includes at least phosphorescence and fluorescence. Therein, the mentioned contact between the at least one sensor substance and the sample is such that the sensor substance can react to the variable of the sample to be determined. If the variable for example is a temperature of the sample, a heat transfer between the sample and the sensor substance must be possible. If the variable to be determined for example is the concentration of a substance, a corresponding contact of substances between the sample and the sensor substance must be possible, meaning that molecules of the sensor substance must meet molecules of the substance, for example to transfer energy between the molecules or for a chemical reaction.

The sensor substance then is excited to luminescence by an electromagnetic excitation signal. The electromagnetic excitation signal has a pre-defined time-dependence. The excitation signal has signal maxima consecutive in time, wherein the temporal distance of consecutive signal maxima decreases or increases over the duration of the excitation signal. The decrease or increase, respectively, of the temporal distance of consecutive signal maxima preferentially is monotonic, particularly preferentially strictly monotonic. Preferentially all signal maxima correspond to the same value of the excitation signal, within tolerances specific to the art.

The method according to the invention in principle always can be used, if there is a sensor substance which can be excited by electromagnetic radiation to show a luminescence phenomenon, as long as this luminescence phenomenon has a relaxation time depending on the variable of the sample to be determined. The wavelength range of the electromagnetic radiation used for excitation is determined by the requirements of the respective sensor substance, i.e. that wavelength range is to be used which can excite the luminescence of the sensor substance used for determining the variable. Those skilled in the art know that the wavelength range preferentially is limited in such a manner that further effects which disturb the determination of the variable, for example by additional luminescence phenomena or a quick destruction of sensor substance or sample, are avoided. The invention therefore is not limited to a specific portion of the electromagnetic spectrum; in the majority of cases electromagnetic radiation ranging from infrared to ultraviolet is used, but the method according to the invention may for example also be used in the range of radio waves, microwaves, terahertz radiation, X-rays and gamma rays. Nor is the method according to the invention limited to the electromagnetic radiation of the luminescence response of the sensor substance being from a specific portion of the electromagnetic spectrum; the luminescence wavelength regions occurring may differ depending on the sensor substance used, the variable to be determined, and the radiation used for excitation.

The time-dependence of the luminescence response of the at least one sensor substance to the excitation signal is captured and integrated over consecutive time-intervals of a given constant duration during the excitation signal. The result of integration over one time-interval yields a value of a further signal, which henceforth will be referred to as output signal. Consecutive values of the output signal, respectively corresponding to the integration over one of the consecutive time-intervals, result in a time-dependence of the output signal. Usually a detector receiving luminescence radiation from the at least one sensor substance is used for capturing the luminescence response. Usually an electrical signal is generated out of the received luminescence light by the detector. The integration mentioned above then may be done by integration of this electrical signal. Depending on the type of detector, however, also an accumulation of the captured luminescence light may be done over a specific time-interval within the detector, and the detector may generate an electrical signal which is a measure for the total energy of luminescence light received within the time-interval. This accumulation may also be the integration. Longer time-intervals of integration may then be obtained by summation over the values of the signal generated by the detector from the accumulation. The duration of a time-interval for integration is at least long enough for the integration to capture the luminescence response of the sensor substance corresponding to a signal maximum of the excitation signal. With detectors having a reaction time larger than the distance of consecutive signal maxima, the luminescence response to a plurality of signal maxima of the excitation signal is captured during a time-interval for integration. Of course this applies also if the duration of the time-intervals for integration is set to a correspondingly long value by a user of the method.

If the excitation signal is such that the temporal distance of consecutive signal maxima decreases, this temporal distance reaches and subsequently falls below a value at which a complete decay of the luminescence of the sensor substance between consecutive signal maxima no longer is possible. This leads to the occurrence of a step or a jump to a higher value in the output signal.

If the excitation signal is such that the temporal distance of consecutive signal maxima increases, this temporal distance reaches and subsequently rises above a value at which a complete decay of the luminescence of the sensor substance between consecutive signal maxima is possible. This leads to the occurrence of a step or a jump to a lower value in the output signal. Complete decay of the luminescence here always means that the luminescence signal has fallen to a value which no longer can be detected, for example, because the value is not above the detector noise.

From the position of this step in the time-dependence of the output signal, i.e. from the instant of the occurrence of the step in the output signal, relative to the time-dependence of the excitation signal, the value of the variable of the sample to be determined can be inferred.

Away from the steps just mentioned the output signal may be, but not necessarily is, constant. If the detector is fast enough, and the time-intervals for integration are short enough, to generate a value of the output signal for each signal maximum of the excitation signal, then in each time-interval for integration in principle integration is over the same time-dependence of the luminescence response. For each time-interval for integration then the same value of the output signal results. With slower detectors and/or longer time-intervals for integration a reduction of the distance of consecutive signal maxima implies that over the course of the excitation signal more and more signal maxima with corresponding luminescence responses are within one time-interval for integration. This leads to a corresponding increase of the output signal. Analogously, with increasing distances between the signal maxima of the excitation signal a decrease of the output signal results. This increase or decrease, respectively, is, however, clearly distinct from the previously mentioned steps in the output signal. This distinction can be made even clearer, if, instead of the output signal, the output signal divided by the number of signal maxima per time-interval for integration is used for further evaluation. In this case the values of the output signal thus modified are constant away from the steps. Instead of dividing by the number of signal maxima, the output signal may also be divided by the total energy of the excitation signal falling within a respective time-interval for integration, or by a quantity proportional thereto.

The defined time-dependence of the excitation signal in embodiments is characterized by the excitation signal being a frequency-modulated signal, with the frequency increasing or decreasing over the duration of the excitation signal.

In another embodiment of the method the excitation signal is a sequence of pulses characterized by the distances between pulses decreasing or increasing over the duration of the excitation signal. For example, each distance between pulses may be shorter or longer than its predecessor by a defined absolute value, such as 0.5 microseconds, or by a defined relative value, such as 5 percent. Therein the pulse durations preferentially are constant.

The purpose of the defined time-dependence of the excitation signal, such as a frequency-modulated signal or a sequence of pulses with distances between pulses varying as detailed above, is to eventually reach a saturation of the luminescence of the sensor substance, or to leave the saturated state, respectively. Saturation here refers to a stationary state, wherein the luminescence response no longer changes, i.e. no longer increases or decreases, on average over some sequences of pulse and following distance between pulses, for example 5 to 10 sequences, or more generally on average over some signal maxima. If a sensor substance reaches or leaves saturation, an already mentioned step in the time-dependence of the output signal occurs; when reaching saturation, the step means an increase of the output signal, when leaving saturation, the step means a decrease of the output signal.

Given a sensor substance with a particular relaxation time of the luminescence response, if this sensor substance is excited for example with a sequence of pulses wherein the distances between pulses decrease over the course of time, the luminescence response at first will no longer decay completely within one distance between pulses, so that in reaction to further pulses the intensity of the luminescence response increases on average, and the luminescence response of the sensor substance eventually reaches saturation. With the increase of the luminescence response on average also the output signal obtained by integration over the luminescence response increases, so that a step occurs in the output signal. If, in this example, the luminescence response has reached saturation, the output signal has the value corresponding to the upper, higher-valued end of this step.

Note that the relaxation time of the luminescence response of the sensor substance also corresponds to the reaction time of the sensor substance to the excitation of the luminescence. By "relaxation time of the sensor substance" the relaxation time of that luminescence phenomenon of the sensor substance is meant which respectively is used for determining the variable; with the same meaning also "relaxation time of the luminescence" and "relaxation time of the luminescence response" are used.

If the relaxation time of the sensor substance is shorter than in the case described above, with the same sequence of excitation pulses, the saturation is reached later. Correspondingly, for a longer relaxation time, the saturation is reached earlier.

Therefore, if the relaxation time of the luminescence response of the sensor substance depends on the variable of the sample to be determined, a value of the variable can be inferred from the instant of the occurrence of a step in the output signal.

An effect similar to the case of an excitation signal with decreasing distances between pulses can be achieved by using a frequency-modulated excitation signal the period of which decreases over time.

If instead excitation signals with increasing distances between pulses or increasing periods are used, a step occurs when the luminescence response of the sensor substance leaves saturation.

In the method according to the invention the sensor used is exposed to an excitation energy significantly lower than for example in phase-modulation methods of prior art. From this a reduced photo-bleaching of the sensor results, i.e. the deterioration of the sensor substance used in the sensor, i.e. of a luminescence dye, by the light used for exciting the luminescence is reduced.

Determining a value of the variable from the instant of the occurrence of a step in the output signal preferentially is done by using a previous calibration, in which, for example, the respective instants of the occurrence of a step are determined for a defined excitation signal and samples with known values of the variable to be determined. This information then is provided as calibration data for the further method in suitable form, for example as table, curve interpolating between data points, or function interpolating between data points. Those skilled in the art know that a corresponding evaluation of a measurement using the calibration may also be done in an automatized manner by a data processing system. Calibration may be performed by the user of the method prior to a measurement proper, but also by the manufacturer of the sensor substance or of pertinent measuring devices. The value of the variable being the same, for different excitation signals a step in the output signal in general occurs at different instants relative to the time-dependence of the respective excitation signal. Therefore a calibration is only valid for the defined time-dependence of the excitation signal for which the calibration was performed. The characteristics of the time-dependence of the excitation signal relevant for the method are the distances in time between consecutive signal maxima or the distances between pulses, respectively, as well as the pulse durations. In contrast, the instants of the occurrence of the steps are largely independent of the intensity of the excitation signal.

The required contact, already mentioned above, between the sample and the at least one sensor substance can be achieved in a simple manner by mixing the sensor substance with the sample.

Alternatively, the at least one sensor substance may be fixed at or in a carrier, and this carrier may be introduced into the sample. The carrier may for example be arranged at a wall of a sample container, wherein this wall must be transparent for the wavelengths of electromagnetic radiation used in the method according to the invention, i.e. for the excitation signal and the luminescence response.

In one embodiment of the method according to the invention at least two sensor substances are brought into contact with the sample. The sensor substances therein differ with respect to the relaxation time of their respective luminescence behavior. Relative to the time-dependence of the excitation signal steps occur in the output signal at different instants. In particular, the relaxation times of at least two of the sensor substances may depend on different variables of the sample. The different instants of the occurrence of a step in this case may be used to unambiguously relate a step to a variable.

It is also conceivable that the relaxation times of the at least two sensor substances depend on the same variable, but that the sensor substances differ with respect to a range of values of this variable within which a dependence of the luminescence behavior of the respective sensor substance on the variable shows. In this way this embodiment of the method according to the invention may be used to render a larger range of values of the variable to be determined accessible to measurement. If in this case the relaxation times of the individual sensor substances differ, the differences of the instants of the occurrence of a step in the output signal may be used to relate this step to a particular sensor substance. This may in particular be an advantage in ranges of values of the variable within which more than one of the sensor substances used show a dependence of their respective relaxation time on the variable, especially, if these dependences are of different strength within the range of values in question. Advantageously then that step in the output signal would be used which belongs to the sensor substance showing the most pronounced dependence on the variable within the range of values in question, in order to be able to measure the variable with the highest precision. Alternatively, for each sensor substance a value of the variable may be determined from the related step in the output signal, and the final result for the value of the variable may be determined therefrom by, as the case may be, weighted, averaging.

An example therefor is a combined trace and full-range oxygen sensor, which on the one hand has a high resolution at low oxygen concentrations near 0% O2, but on the other hand can cover the measuring range up to 100% O2. Herein advantageously two luminescence dyes may be used as sensor substances which can be excited to luminescence by the same excitation wavelength, and which also emit in the same spectral region. In this case one excitation light source, for example LED, suffices for both luminescence dyes, and the same optical filters may be used for both luminescence responses.

As trace sensor, with a detection limit of 1 ppb O2 in solution at 20° C. and a measuring range up to 5% O2 in solution, dyes from the class of palladium porphyrins may be used. The excitation wavelength here is 400 nm, the relaxation time varies from 900 microseconds at 0% O2 to 150 microseconds at 5% O2.

As full-range sensor, with a detection limit of 15 ppb O2 in solution at 20° C. and a measuring range up to 100% O2 in solution, dyes from the class of platinum porphyrins may be used. The excitation wavelength here is 400 nm, the relaxation time varies from 60 microseconds at 0% O2 to 10 microseconds at 100% O2.

In this example the measurement may for instance be done with pulses of 10 microseconds duration, wherein the distance between pulses is reduced from 1000 microseconds to 1 microsecond in steps of 1 microsecond.

In principle the luminescence response of all sensor substances in contact with the sample may be captured with a common detector. A prerequisite therefor is that the detector is sensitive to the wavelengths of all occurring luminescence responses.

Likewise more than one detector may be used for capturing the luminescence responses of all sensor substances. Each detector used captures the luminescence responses of a part of the sensor substances, each detector captures at least the luminescence response of at least one sensor substance. The signals generated by the individual detectors out of the luminescence light may then be summed to obtain a resulting signal, which then is further evaluated as described above. It is likewise possible to evaluate the signals from the individual detectors separately.

As detector in particular a photodiode may be used. Alternatively, imaging sensors based on CMOS or CCD may be used.

The method may be performed advantageously in parallel for a plurality of samples by bringing each sample separately in contact with at least one sensor substance, exposing the sensor substances of all samples together to an electromagnetic excitation signal, separately capturing the luminescence response of each sample, and evaluating it as already described above. Therein the same sensor substance may be used for each sample. It is, however, also possible that for at least two samples the sensor substances in contact with theses samples differ. In particular, different variables can be determined for the individual samples. Separately capturing the luminescence responses of the samples may, in case an imaging sensor is used as detector, be done by capturing an image sequence of an arrangement of the samples; in the images of the sequence each sample can be identified, of course in an automatized manner or by defining image areas corresponding to the respective sample. Capturing the luminescence response of the respective sample then is done via the pixel values pertaining to the respective image areas.

In a further embodiment of the method, at least one sensor substance is brought into contact with the sample, and the sensor substance is repeatedly excited to luminescence by an excitation signal of the kind described above. The pertinent luminescence response is respectively captured. For each luminescence response a value of the variable to be determined may be derived, and a resulting value of this variable then be determined by averaging over these values for the individual luminescence responses. Alternatively, the instants at which steps occur in the output signals obtained for the individual luminescence responses may be averaged, and a resulting value of the variable then is determined from the result of this averaging.

The method according to the invention may be used for determining any variable for which there are sensor substances showing a luminescence behavior which depends on the variable to be determined. In particular, the variable may be a concentration of a substance, a pressure, a temperature, a partial pressure of a gas, or a pH-value. Those skilled in the art thus know a plenitude of suitable sensor substances, with which the method according to the invention may be performed.

As light sources light sources known for exciting optical sensors may be used, for example LEDs or lasers.

BRIEF DESCRIPTION OF THE DRAWINGS

Below the invention will be illustrated further by embodiments and the accompanying schematic drawings.

DETAILED DESCRIPTION

Figure 1:
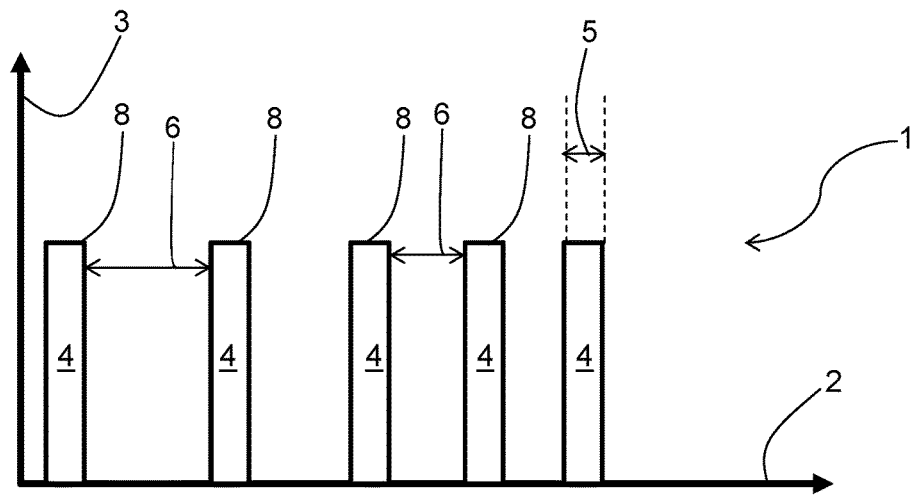
FIG. 1 shows an excitation signal which is a sequence of pulses.

FIG. 1 shows an excitation signal 1, which is a sequence of pulses, as may be used for exciting a luminescence of a sensor substance in the method according to the invention. Time is shown on the abscissa 2, the ordinate 3 shows a measure for the strength of the excitation signal 1, for example the intensity of the excitation signal 1. The excitation signal 1 comprises a sequence of pulses 4, and is characterized by pulse durations 5 and distances 6 between pulses. In the sequence of pulses shown, the pulse durations 5 are constant over the duration of the sequence of pulses, the distances 6 between pulses, however, decrease from pulse 4 to pulse 4. The sum of pulse duration 5 and distance 6 between pulses for the rectangular pulses shown here corresponds to the temporal distance of consecutive signal maxima 8. The decreasing distances 6 between pulses therefore imply that the distances between consecutive signal maxima 8 of the excitation signal 1 decrease over the duration of the excitation signal 1.

The method according to the invention could also be performed with pulse shapes different from rectangular pulses, for example sawtooth pulses or pulses with Gaussian profile, as will be apparent to those skilled in the art from the above disclosure.

The pulse durations and distances between pulses to be used essentially are determined by the relaxation times of the sensor substances used. Typical pulse durations and distances between pulses range from 100 picoseconds to 2000 microseconds, without this constituting a limitation of the invention. Advantageously the longest distance between pulses used should be long enough that for the longest expected relaxation time of a luminescence a complete decay of this luminescence is possible, for example the longest used distance between pulses may be three times to five times the longest expected relaxation time. The shortest used distance between pulses should be considerably shorter than the shortest expected relaxation time of a luminescence, so that also for the luminescence response pertaining to the shortest expected relaxation time saturation is quickly reached by action of the excitation signal. For example, the shortest used distance between pulses may be one tenth of the shortest expected relaxation time.

Figure 2:
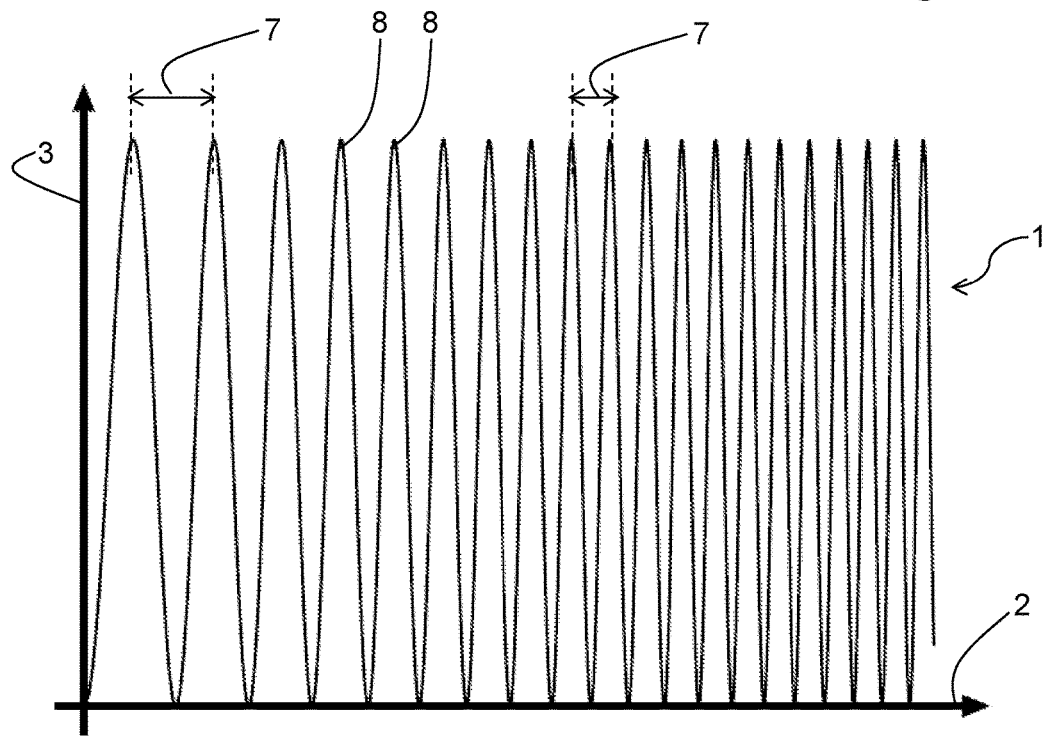
FIG. 2 shows a frequency-modulated signal, which is a further possible kind of an excitation signal.

FIG. 2 shows an excitation signal 1, which is a frequency-modulated signal, as may be used for exciting a luminescence of a sensor substance in the method according to the invention. Time is shown on the abscissa 2, the ordinate 3 shows a measure for the strength of the excitation signal 1, for example the intensity of the excitation signal 1. Over the course of the excitation signal 1 the period 7 of the excitation signal 1, which here is shown to be of sine-shape, decreases, correspondingly the distance between consecutive signal maxima 8 of the excitation signal 1 decreases. The distance between consecutive signal maxima 8 of the excitation signal 1 here is equal to the period 7.

Figure 3:
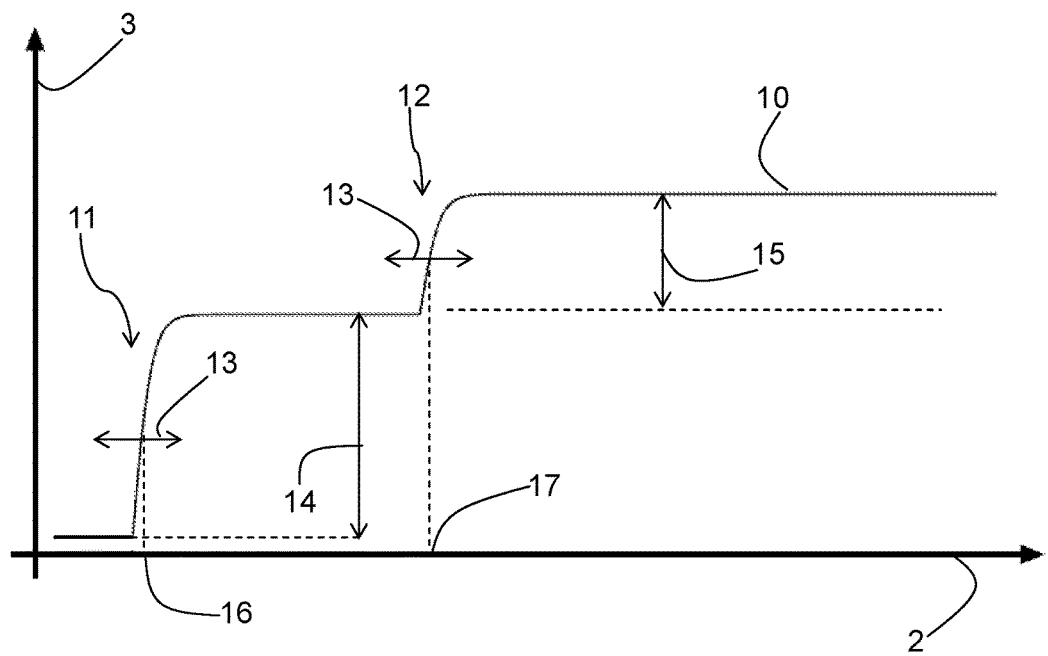
FIG. 3 shows a time-dependence of an output signal.

FIG. 3 shows the time-dependence of an output signal 10, if two sensor substances, a first sensor substance and a second sensor substance, are used in a sample, wherein the sensor substances are excited to luminescence by an excitation signal according to the method according to the invention, wherein the temporal distances between consecutive signal maxima in the excitation signal decrease. Time is shown on the abscissa 2, the ordinate 3 shows a measure for the value of the output signal 10.

In the time-dependence of the output signal 10 a first step 11 and a second step 12 are visible. In the first step 11 the first sensor substance reaches a saturation of its luminescence, in the second step 12 the second sensor substance reaches a saturation of its luminescence. The relaxation time of the second sensor substance, in the example shown here, is shorter than the relaxation time of the first sensor substance.

For the same excitation signal the instant 16, 17 of the occurrence of a step 11, 12 depends on a variable of the sample to be determined, because the relaxation times of the sensor substances depend on the variable; this means that the position of a step 11, 12 on the abscissa 2 shifts depending on the value of the respective variable. This is indicated by double arrows 13. As instant 16 of the occurrence of the first step 11 and as instant 17 of the occurrence of the second step 12, respectively, here that instant is chosen, at which the respective step 11, 12 has reached half its height 14, 15. Other definitions for defining the instant of the occurrence of a step are also possible. Herein it is important that identical definitions for defining the instant of the occurrence of a step are used for calibration and measurement. Furthermore, the instant 16, 17 of the occurrence of a step is always related to the time-dependence of the excitation signal, for example, the instant of the onset of the excitation signal may be chosen as the origin of the time-axis on which also the instant 16, 17 of the occurrence of a step is specified.

The height of the steps occurring in the output signal may be different. In the example shown, the height 14 of the first step 11 is greater than the height 15 of the second step 12.

In the example shown here, the value of the excitation signal 10 away from the steps 11, 12 is constant. As already described above, this results in the case of short time-intervals for integration and fast detectors, i.e. detectors with short reaction times in comparison with the temporal distance of consecutive signal maxima of the excitation signal.

Figure 4:
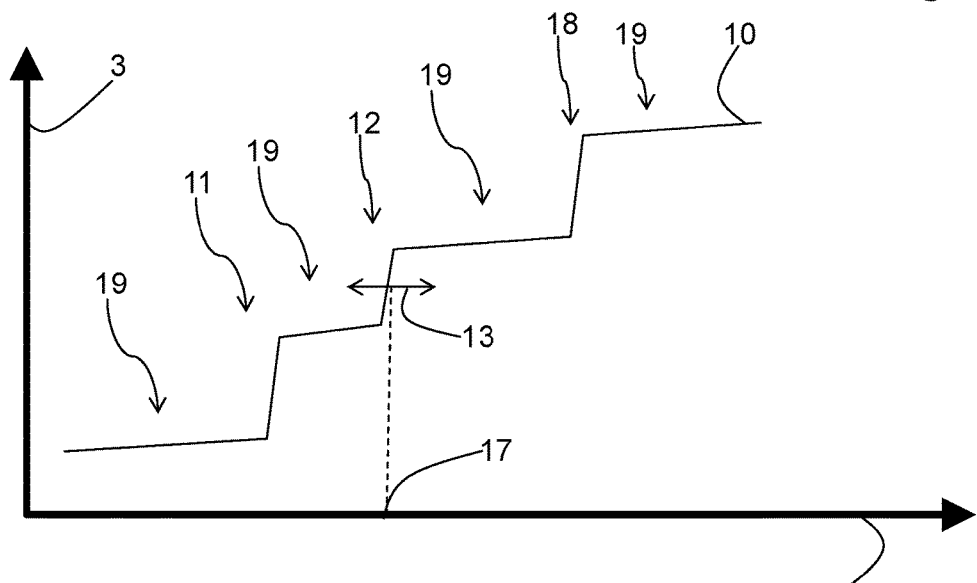
FIG. 4 shows a further example of a time-dependence of an output signal.

FIG. 4 shows a further example for the time-dependence of an output signal 10. The time-dependence shows three steps 11, 12, 18, as well as areas 19 with a flatter slope of the output signal 10. As explained above, the areas 19 of flatter slope result, because, with decreasing distance of consecutive signal maxima of the excitation signal, more and more signal maxima lie within a time-interval for integration. By dividing the output signal 10 by the number of signal maxima respectively lying within a time-interval for integration, or by a quantity proportional thereto, a modified output signal, having a constant value in the areas 19 between the steps, results.

The instants of the occurrence of the steps 11, 12, 18 may be determined for the time-dependence of the output-signal 10 shown in FIG. 4, too, in analogy to the case shown in FIG. 3. As an example, this is shown here for step 12 with pertinent instant 17.

The details of the time-dependence of the output signal 10 away from the steps 11, 12, 18, and likewise the precise shape of the steps 11, 12, 18, depend on particulars of the measuring method, like for example the reaction time of the detector used and the length of the time-intervals for integration. What is relevant for the method according to the invention, however, is the occurrence of the steps 11, 12, 18 and the dependence of the instant of the occurrence of these steps on the variable to be determined.

Figure 5:
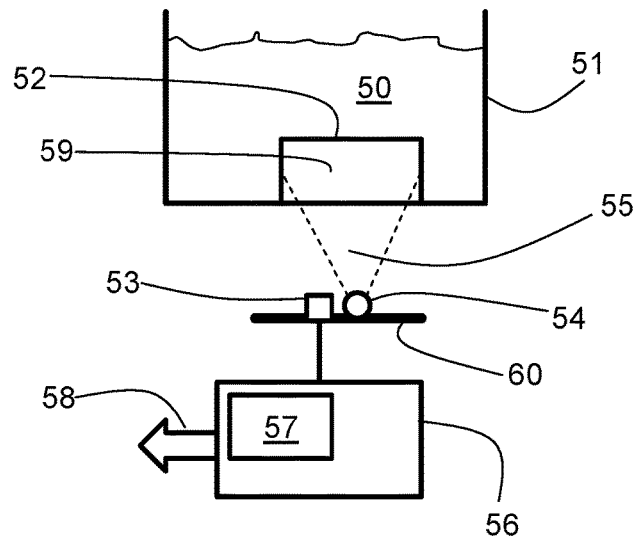
FIG. 5 shows the arrangement of a carrier for the sensor substance in a sample container and an example of the configuration of an apparatus for performing the method according to the invention.

FIG. 5 shows a sample 50 in a sample container 51. A carrier 52, provided with a sensor substance 59, which is in contact with the sample 50, is arranged in the sample container 51. For example, the carrier 52 may be soaked with the sensor substance 59.

A photodiode 53 and a light source 54 are located outside of the sample container 51, in the arrangement shown on a board 60. The light source 54, here an LED, emits an electromagnetic excitation signal of the kind described above in the form of light 55, in order to excite the sensor substance 59 to luminescence. The photodiode 53 receives luminescence light from the sensor substance 59 and generates an electrical signal therefrom. Depending on the performance of the method and the reaction time of the photodiode 53, this electrical signal may already be the output signal within the meaning of this application, or an evaluation unit 56 generates the output signal from this electrical signal by integration over defined intervals. The evaluation unit 56 then determines the instants of the occurrence of steps in the output signal. With the help of calibration data 57 provided previously, the evaluation unit 56 then determines the value of a variable of the sample 50. The thus determined value of the variable of the sample 50 is sent to an output 58, for example to a user via a display, or to a downstream data processing system. The light source 54 may also be controlled by a downstream data processing system; it is also possible to integrate a control system for the light source 54 into the evaluation unit 56.

Note that the arrangement of light source 54 and photodiode 53 here is only an example. The same applies to the position of the carrier 52 within the sample container 51. In the example shown the sample 50 is liquid, which does not constitute a limitation of the invention, either. Gaseous sample may be analyzed, as well.

Figure 6:
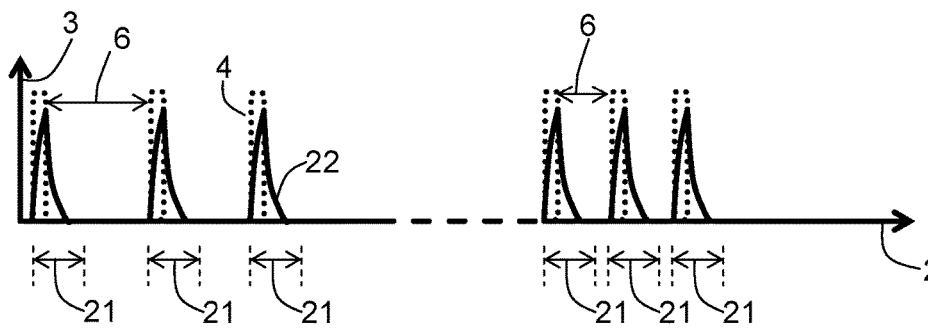
FIG. 6 shows time-intervals for integration in relation to excitation pulses and a corresponding luminescence response of the sensor substance.

FIG. 6 shows time-intervals 21 for integration, and pulses 4 (dotted) of an excitation signal with distances 6 between pulses decreasing over the duration of the excitation signal, in analogy to FIG. 1. Further shown is the luminescence response 22 to each pulse 4. During the duration of a pulse 4 the luminescence response 22 increases, after the end of the respective pulse 4 the luminescence response 22 decays. Time is shown on the abscissa 2, the ordinate 3 shows a measure for the strength of the excitation signal and of the luminescence response 22. The time-intervals 21 for integration, which are consecutive during the duration of the excitation signal, here during the sequence of pulses 4, have a constant length, which here is such that rise and decay of the luminescence response 22 to a pulse 4 can just occur within a time-interval 21 for integration. The position in time of the time-intervals 21 for integration here is correlated with the pulses 4, more precisely, the integration over the luminescence response 22 is triggered by a respective pulse 4. The integration of the luminescence response 22 over each of the time-intervals 21 for integration shown yields here the same value, even if in the later course of the excitation signal, separated from the initial phase of the excitation signal by a dashed section of the abscissa, the distance 6 between pulses is significantly reduced in comparison with the initial value. The output signal 10 (see FIGS. 3 and 4) formed by the results of the integration over the individual time-intervals 21 for integration, has a constant value for the period of time shown on the abscissa. For a further pulse 4 and correspondingly a related luminescence response 22 to lie within the time-interval 21 for integration pertinent to the preceding pulse 4, here the distance 6 between pulses would have to be reduced to such an extent that a complete decay of the luminescence response 22 within the distance 6 between pulses is hardly possible any longer. This, however, is the first step to the formation of a saturated luminescence signal, and thus the transition to a step in the output signal 10.

Figure 7:
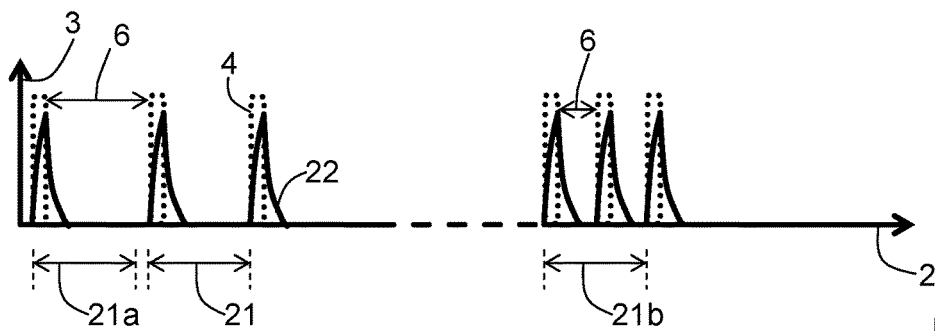
FIG. 7 also shows time-intervals for integration in relation to excitation pulses and a corresponding luminescence response of the sensor substance, wherein the time-intervals for integration are longer than in FIG. 6.

FIG. 7 largely corresponds to FIG. 6, only the time-intervals 21 for integration are longer here than in the case of FIG. 6. In the case of FIG. 7, too, each time-interval 21, 21a, 21b for integration is of equal length. Now the situation occurs, however, as shown for time-interval 21b for integration, that the luminescence response 22 can completely decay within a distance 6 between pulses, but that there is already more than one pulse 4 with corresponding luminescence response 22 within the time-interval for integration. There are two pulses 4 with corresponding luminescence response 22 within the time-interval 21b for integration, there is one pulse 4 with corresponding luminescence response 22 in the time-interval 21a for integration. Correspondingly, on integration over the interval 21b a value for the output signal 10 results, which is twice the value resulting on integration over interval 21a. The period of time shown on the abscissa 2 in FIG. 7 thus corresponds to an area 19 in FIG. 4, in which, away from a step 11, 12, 18, the output signal 10 increases. In this case, too, the integration may be triggered by a pulse 4, however only by a pulse 4 not falling within a time-interval for an integration triggered by one of the preceding pulses.

The duration of the time-intervals 21 for integration is pre-defined, it is either explicitly given by a user of the method according to the invention, or determined by the choice of the detectors, used for capturing the luminescence response 22, via their reaction time.

What is claimed is:
1. A method for determining a variable of a sample, comprising the steps of:
   a) establishing a contact between at last one sensor substance and the sample, wherein the at least one sensor substance has a luminescence behavior with a relaxation time depending on the variable;

b) exciting the luminescence behavior of the at least one sensor substance by an electromagnetic excitation signal exhibiting a pre-defined time-dependence with consecutive signal maxima, wherein a temporal distance of consecutive signal maxima either decreases monotonically over the duration of the excitation signal or increases monotonically over the duration of the excitation signal;

c) generating a time-dependent output signal by integration of a time-dependence of a luminescence response of the at least one sensor substance to the excitation signal over consecutive time-intervals during the excitation signal; and d) determining the variable from at least one instant of time, relative to the time-dependence of the excitation signal, of the occurrence of a step in the output signal.

2. The method as recited in claim 1 wherein, for determining the instant of the occurrence of the step, the output signal is modified by dividing the output signal by the number of signal maxima within a time-interval for the integration or by the energy of the excitation signal falling within a time-interval for the integration.

3. The method as recited in claim 1 wherein the excitation signal is a frequency-modulated signal, the frequency of the frequency-modulated signal increasing or decreasing over time.

4. The method as recited in claim 1 wherein the excitation signal is a sequence of pulses, with distances between pulses decreasing or increasing over the course of the excitation signal.

5. The method as recited in claim 1 wherein the determining the variable according to step d is done taking into account given calibration data.

6. The method as recited in claim 1 wherein the at least one sensor substance is mixed with the sample.

7. The method as recited in claim 1 wherein a carrier provided with at least one of the sensor substances is introduced into the sample.

8. The method as recited in claim 1 wherein the luminescence response of all sensor substances in contact with the sample is captured by a common detector.

9. The method as recited in claim 8 wherein a photodiode or an optoelectronic imaging sensor is used as the common detector.

10. The method as recited in claim 1 wherein at least two sensor substances of the at least one sensor substance are brought into contact with the sample, the sensor substances differing with respect to a relaxation time of the luminescence behavior of the sensor substances.

11. The method as recited in claim 10 wherein more than one detector is used for capturing the luminescence response, and each detector captures the luminescence response of a part of the sensor substances.

12. The method as recited in claim 11 wherein a photodiode or an optoelectronic imaging sensor is used as the detectors.

13. The method as recited in claim 10 wherein the at least two sensor substances differ with respect to the variable, the relaxation time of the luminescence behavior of the respective sensor substance depending on the variable.

14. The method as recited in claim 10 wherein the at least two sensor substances differ with respect to a range of values of the variable, a dependence of the luminescence behavior of the respective sensor substance on the variable showing within the range of values of the variable.

15. The method as recited in claim 1 wherein the method is performed for a second sample, by performing the steps a, c, d for the sample and the second sample separately, and exciting the sensor substances of the sample and the second sample according to step b by an electromagnetic excitation signal, the sensor substances of the sample and second sample being exposed together.

16. The method as recited in claim 1 wherein the steps b and c are performed repeatedly, and a resulting value of the variable is determined by averaging.

17. The method as recited in claim 1 wherein the at least one variable is a concentration of a substance, a pressure, a temperature, a partial pressure of a gas, or a pH-value.

18. A method for determining a variable of a sample comprising the steps of:
a) establishing a contact between at least one sensor substance and the sample, wherein the at least one sensor substance has a luminescence behavior with a relaxation time depending on the variable;
b) exciting the luminescence behavior of the at least one sensor substance by an electromagnetic excitation signal comprising a sequence of pulses, wherein each distance between consecutive pulses of the sequence is shorter by a fixed amount than its predecessor;
c) generating a time-dependent output signal by integration of a time-dependence of a luminescence response of the at least one sensor substance to the excitation signal over consecutive time-intervals during the excitation signal, wherein each integration is triggered by a pulse of the excitation signal; and
d) determining the variable from at least one instant of time, relative to the time-dependence of the excitation signal, of the occurrence of a step in the output signal.

19. A method for determining a variable of a sample comprising the steps of:
a) establishing a contact between two sensor substances and the sample, each of the two sensor substances having a luminescence behavior with a relaxation time depending on the variable, wherein the two sensor substances differ with respect to a range of values of the variable within which a dependence of the relaxation time of the luminescence behavior of the respective sensor substance on the variable shows;
b) exciting the luminescence behavior of the two sensor substances by an electromagnetic excitation signal comprising a sequence of pulses, wherein each distance between consecutive pulses of the sequence is shorter by a fixed amount than its predecessor;
c) generating a time-dependent output signal by integration of a time-dependence of a luminescence response of the two sensor substances to the excitation signal over consecutive time-intervals during the excitation signal, wherein each integration is triggered by a pulse of the excitation signal; and
d) determining the variable from at least one instant of time, relative to the time-dependence of the excitation signal, of the occurrence of a step in the output signal.

20. The method of claim 19 wherein a full range of values over which the relaxation time of the luminescence behavior of a first sensor substance of the two sensor substances varies in dependence on the variable does not overlap with a full range of values over which the relaxation time of the luminescence behavior of a second sensor substance of the two sensor substances varies in dependence on the variable.

* * * * *